United States Patent
Burg et al.

(10) Patent No.: US 6,666,893 B2
(45) Date of Patent: Dec. 23, 2003

(54) ABSORBABLE TISSUE EXPANDER

(75) Inventors: Karen J. L. Burg, Mt. Holly, NC (US); Craig Reed Halberstadt, Charlotte, NC (US); Walter Dalton Holder, Jr., Charlotte, NC (US)

(73) Assignee: Charlotte-Mecklenburg Hospital, Charlotte, NC (US)

( * ) Notice: Subject to any disclaimer, the term of this patent is extended or adjusted under 35 U.S.C. 154(b) by 0 days.

(21) Appl. No.: 09/819,847

(22) Filed: Mar. 28, 2001

(65) Prior Publication Data

US 2002/0010514 A1 Jan. 24, 2002

Related U.S. Application Data

(62) Division of application No. 09/131,470, filed on Aug. 10, 1998, now Pat. No. 6,206,930.

(51) Int. Cl.$^7$ .................................................. A61F 2/02
(52) U.S. Cl. ...................... 623/23.75; 623/8; 623/23.64; 623/23.67; 623/23.76
(58) Field of Search ...................... 623/8, 23.64, 23.67, 623/23.75, 23.76

(56) References Cited

U.S. PATENT DOCUMENTS

| | | | |
|---|---|---|---|
| 4,925,446 A | | 5/1990 | Garay et al. |
| 5,413,571 A | | 5/1995 | Katsaros et al. |
| 5,549,679 A | | 8/1996 | Kuslich |
| 5,578,085 A | * | 11/1996 | Johnson, Jr. et al. ......... 623/11 |
| 5,634,936 A | | 6/1997 | Linden et al. |
| 5,716,404 A | | 2/1998 | Vacanti et al. |
| 6,066,856 A | * | 5/2000 | Fishman .................. 250/519.1 |
| 6,228,116 B1 | * | 5/2001 | Ledergerber .................. 623/8 |

* cited by examiner

*Primary Examiner*—David H. Willse
*Assistant Examiner*—Javier G. Blanco
(74) *Attorney, Agent, or Firm*—Alston & Bird LLP

(57) ABSTRACT

A method of reconstructing tissue is provided. The method includes implanting an absorbable tissue expander having a fluid-tight or semipermeable envelope and having a bioabsorbable biocompatible shell defining a chamber. The envelope is inflatable upon infusion of a fluid into the chamber and deflatable upon removal of the fluid from the chamber. The tissue expander also has an injection port for the controlled inflation and deflation of the envelope after the device is implanted in a tissue. The method also may include a plurality of envelopes.

9 Claims, 2 Drawing Sheets

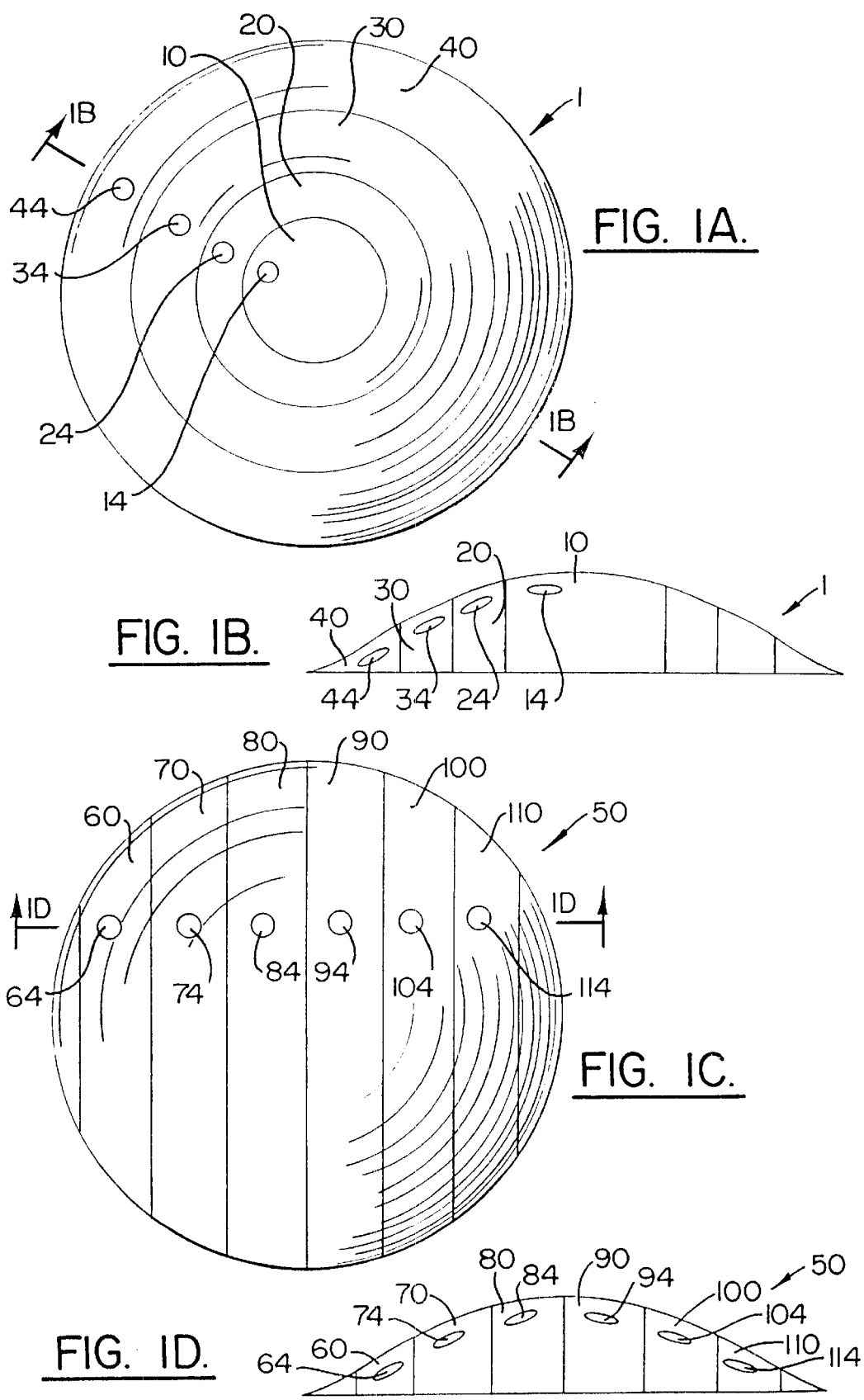

ABSORBABLE TISSUE EXPANDER

CROSS-REFERENCE TO RELATED APPLICATIONS

This application is a division of U.S. application Ser. No. 09/131,470, now U.S. Pat. No. 6,206,930 B1 filed Aug. 10, 1998, which is hereby incorporated herein in its entirety by reference.

FIELD OF INVENTION

The present invention generally relates to a tissue expander and method of using the same.

BACKGROUND OF THE INVENTION

Tissue expanders are well known in the art. Traditional tissue expanders are temporarily implanted beneath skin and subcutaneous tissue of humans or animals to create a void or pocket or to stretch the skin. The implanted device is gradually inflated by injecting therein fluid or gel to force the surrounding and overlying skin to expand. Once the skin is expanded and a skin flap has formed, the device is deflated and surgically removed. A permanent, implantable device such as a mammary implant or prosthesis may be placed surgically beneath the skin flap. The expanded skin can also be excised and used in repairing a defective area in another part of the body. For detailed description of tissue expanders, see, e.g., Cohen, *J. Dermatol. Sur. Oncol.* 19:614–615 (1993); Hammond, et. al., *Plastic and Reconstructive Surgery*, 92(2):255–259 (1993); Walton and Brown, *Annals of Plastic Surgery* 30(2):105–110 (1993); Kenna, et al., *Annals of Plastic Surgery* 32:346–349 (1994). Tissue expanders have also been used in other surgery procedures. For example, tissue expanders may be implanted and inflated at a bleeding site to maintain pressure on the surface to prevent further bleeding while clotting and healing takes place. In addition, tissue expanders have also been implanted within the pelvis of patients who have had some or all of the pelvic contents removed due to cancer. In this situation, the expander excludes the small bowel from the pelvis. As a result, the small bowel which is sensitive to ionizing radiation is excluded from subsequent radiation treatment fields. See, e.g., Keno et. al., *Oncology*, 12(1): 51–54 (1998).

In the above described applications, because the purpose is to stretch or force tissue apart or to simply fill a void, the deflation and removal of the expander generally does not significantly disrupt the surrounding areas and does not cause substantially adverse effect. Nevertheless, the removal of the expander may require an additional surgical procedure.

Tissue expanders have also been used in tissue reconstruction which involves increase of new tissue mass. For example, U.S. Pat. No. 5,716,404 to Vacanti et al. teaches applying traditional expanders in breast reconstruction involving cell transplantation. In this application, cells are injected into the area where new tissue is desired. Prior to the injection, the space for accommodating these cells is created using a tissue expander. The tissue expander is implanted in a collapsed configuration, and is then inflated by introducing therein liquid or gel. Prior to each subsequent injection of cells, the tissue expander is deflated to vacate a space equivalent to the volume of the cell suspension to be injected. Once the space is filled with cell suspension or new tissue, the tissue expander is surgically removed using anesthetic incisions.

SUMMARY OF THE INVENTION

In reconstructive applications, removal of the expander could be potentially problematic as new tissue grows and surrounds the slowly deflating expander. The retrieval of such a device may disrupt newly developed tissue and become counterproductive. On the other hand, in traditional expander applications as fillers or expanders, disruption of new tissue usually is not a concern. Yet, removing the expander may require complex surgical procedures.

The absorbable tissue expander device of this invention successfully solves these problems. It would maintain mechanical integrity for a desired period of time and would gradually absorb to complete loss of mass, thus requiring no removal procedure.

Accordingly, an absorbable tissue expander and methods of using the device are provided in accordance with the present invention. The bioabsorbable tissue expander comprises a fluid-tight envelope and means for the controlled inflation and deflation of said envelope after the device is implanted in a tissue. The envelope has a bioabsorbable biocompatible shell defining a chamber. The envelope is inflatable upon infusion of fluid into the chamber and is deflatable upon withdrawal of fluid from the chamber or by release of fluid into the surrounding area through the shell as a result of biodegradation. Examples of suitable bioabsorbable materials for making the shell include but are not limited to polyesters, polyanhydrides, polyurethanes, polyphosphazenes, polyorthoesters, polyoxalates, polycaprolactone, copolymers of lactide and ecaprolactone, polyetheresters, polycarbonates, polyamides, polyacetals, polycyanoacrylates, polyethylene oxide, and elastomeric polypeptides.

The inflation and deflation means may include any conventional designs known in the art, e.g., injection ports having a hollow region which is in fluid communication with the interior of a chamber, or a self-sealing means comprising injecting or removing fluid from the chamber with a needle penetrating through the shell and self-sealing of the shell by the flowing together of shell wall material at the needle hole. Additionally, the deflation may be caused by the release of fluid across the shell wall of the expander as a result of the gradual biodegradation of the shell wall. The fluid used typically is liquid or gel, e.g. saline liquid. Materials for modifying cell growth such as growth factors may also be included in the envelope, either associated with the shell wall or simply mixed in the fluid or gel.

In a preferred embodiment, the absorbable tissue expander of the present invention has a plurality of fluid-tight envelopes. Each envelope has a chamber defined by a bio-absorbable biocompatible shell. Each envelope also has a separate means for controlled inflation and deflation of the envelope after the device is implanted in a tissue. In addition, each envelope is processed to have unique mechanical properties and mass loss profile. Therefore, it is possible to allow sequential deflation of the envelopes and sequential absorption of the shell material.

The present invention further provides a method of reconstructing a tissue using the absorbable tissue expander of the present invention. In the method, the device is implanted in the tissue to be reconstructed and the envelope(s) is inflated with biocompatible liquid or gel to create a space for the growth of new tissue. As the tissue surrounding the envelopes grows, the envelopes are gradually deflated or degraded so as to provide space for further tissue development until the envelopes are completely deflated and gradually absorbed by the developed tissue.

In accordance with another embodiment of the present invention, a method of adjusting the position of an organ or tissue inside the body of a living subject is provided. An absorbable tissue expander of the present invention is implanted in proximity to the organ or tissue and is thereafter inflated to contact or dislocate the organ or tissue. In a preferred embodiment, the method is used to exclude the small bowel from a radiation treatment field. The absorbable tissue expander is preferably deflated by means of biodegradation of the expander material while allowing for its fluid contents to disseminate into the surrounding body cavity.

Absorbable expanders can also be designed to release a wide variety of biologicals over time including cytokines, growth factors, antineoplastic, chemotherapy agents, adhesion preventing agents and the like.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF DRAWINGS

FIG. 1A illustrates a top view of an embodiment of the absorbable tissue expander showing four envelopes;

FIG. 1B is a cross-section view of FIG. 1A taken along lines 1B—1B;

FIG. 1C illustrates a top view of another embodiment of the absorbable tissue expander showing a plurality of envelopes;

FIG. 1D is a cross-section view of FIG. 1C taken along lines 1D—1D;

DETAILED DESCRIPTION OF THE INVENTION

Figure 2A:
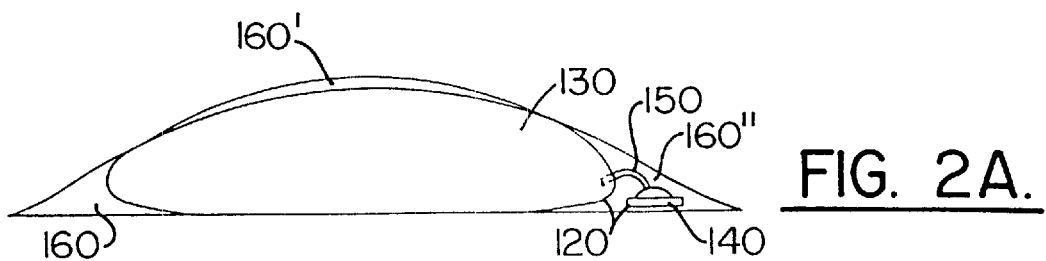
FIG. 2A depicts a side view showing the tissue expander device of the present invention implanted beneath the skin and subcutaneous tissue.

The present invention provides an absorbable tissue expander implantable in a tissue in humans or animals comprising a fluid-tight envelope and means for the controlled inflation and deflation of the envelope after the device is implanted in the tissue. The envelope has a chamber defined by a bio-absorbable biocompatible shell, and optionally may contain signals for modifying cell growth. The envelope is inflatable upon infusion of fluid into the chamber and is deflatable upon withdrawal of fluid from the chamber either by physical removal of the fluid or through the breakdown of the shell with a concomitant release of the fluid into the surrounding body cavity. The fluid used is preferably a biocompatible liquid or gel, and optionally may contain signals such as growth factors. Alternatively, the membrane can be engineered to render it semipermeable, permitting continuous gradient release of growth factors or other substances.

By "biocompatible" is intended that the material or composite of materials used for making the absorbable tissue expander does not substantially adversely affect the body and tissue of the living subject in which the device is implanted. More particularly, the material does not substantially adversely affect the growth and any other desired characteristics of the tissue cells surrounding the implanted device. It is also intended that the material used does not cause any substantially medically undesirable effect in any other areas of the living subject. In addition, because the material will eventually be absorbed by tissue, the degradation product of the material should also be substantially biocompatible as defined above. Generally, the methods for testing a material's biocompatibility is well known in the art.

The biocompatible material used for the present invention is also bio-absorbable, and will be gradually degraded inside the tissue of a living subject. Such degradation should be in a slow and gradual and controlled fashion. For example, the expander of the present invention may be designed such that substantial degradation does not occur until after sufficient new tissue is formed and the envelope is substantially deflated by removing substantially all the liquid or gel within the chamber. In this manner, the degradation of the bio-absorbable material does not result in any significant leakage of liquid or gel from the envelope. Alternatively, bio-absorption may occur at an early stage. This is desirable where the deflation of the envelope is by means of releasing the fluid through the degraded shell wall. Early bio-absorption is particularly desirable, for example, where growth factors are included in the liquid or gel within the chamber of the tissue expander and certain leakage of the growth factors into the surrounding environment may be desirable to stimulate tissue growth. In that event, degradation of the bio-absorbable material before the expander is substantially deflated may be advantageous. As the shell wall of the expander is gradually degraded, the fluid or gel therein may be gradually released, i.e., leaked through the shell wall. This allows the movement of the growth factors across the shell wall of the envelope into the surrounding tissue as new tissue forms and the expander deflates.

Accordingly, the projected tissue growth rate and the minimum permeability required for growth factors to cross the shell should be taken into account in selecting the bio-absorbable material and in constructing the device. Controlled degradation of the absorbable tissue expander of the present invention can be achieved by proper selection from different types of bio-absorbable materials, or different molecular weights or molecular orientation of the same material. Alternatively, the thickness or density of the shell can also be designed differently for controlled absorption of the expander. Generally speaking, it is acceptable for the bio-absorbable envelope shell to be completely degraded in a period of from about 1 month to about 2 years, more preferably from about 3 months to about 1 year after the device is implanted.

The biocompatible bio-absorbable material for making the implantable device should also possess satisfactory physical properties so that the envelope of the device is capable of maintaining desirable mechanical integrity and physical dimensions. Generally speaking, the material should maintain mechanical strength for a minimum time of approximately one month and a maximum time of approximately two years.

Examples of suitable bio-absorbable materials include but are not limited to polyesters (for example, polylactide, polyglycolide), polyanhydrides, polyphosphazenes, polyorthoesters, polyoxalates, polyetheresters, polyethylene glycols, polycaprolactone, polycarbonates, polyethylene oxide, and elastomeric polypeptides. Suitable examples also include but are not limited to polyvinyl alcohols, polyacrylamides, polyamides, polyacrylates, polyesters, polymethacrylates, polyurethanes, polysaccharides such as dextran, dextrin, starch, cellulose, agarose, carrageenan, chitosan, alginate (a carboxylated seaweed polysaccharide), and the like; synthetic polymers such as copolymers of lactide and glycolide, copolymers of lactide and ε-caprolactone, copolymers of lysine and lactide, copolymers of lysine-RGD and lactide, and the like. Proteins such as collagens, copolymers of collagen and chondroitin sulfate (a proteoglycan component), and the like can also be used. Composites of these materials can also be used. Most preferably, the envelope is made from a polylactide or a copolymer of ε-caprolactone/lactide.

The envelope of the present invention may assume any size and any geometrical configuration, e.g., square, rectangular, circular, oval, semi-sphere, rod, doughnut, kidney, flat base, or cone shaped. The shape of the expanded envelope preferably substantially corresponds to the defect area where the envelope is to be implanted. Complex shapes can be designed for this purpose. For example, the envelope can be designed in a manner that when they are inflated, multiple projections with defined dimensions can be formed as disclosed in U.S. Pat. No. 5,158,571 to Picha which is incorporated herein by reference. Such projections are said to improve non-classical tissue response such as vascularization, and reduce the thickness of the fibrous capsule surrounding the device. Complex shapes can also be formed by having multiple sections in the same envelope having different modulus of elasticity as disclosed in U.S. Pat. No. 4,899,764 to Gauger et al., which is incorporated herein by reference. The shape of the envelopes can also be designed to be adjustable as described in U.S. Pat. No. 5,571,179 to Manders et al., which is incorporated herein by reference.

The size of the envelope of the device will depend on the defect area to be reconstructed. Generally the volume of the envelope can range, for example, from about 1 cm$^3$ to about 1000 cm$^3$. The size of each dimension of the fully inflated device can range from about 0.1 cm to about 100 cm, preferably from about 0.5 cm to about 50 cm, and more preferably from about 1 cm to about 20 cm. It would be apparent for an ordinarily skilled person in the art apprised of the present invention to select suitable dimensional sizes for a particular purpose.

The shell wall of an envelope can be made from a single type of material or from a mixture of different types of material including both permeable and non-permeable materials. Alternatively, different sections of the envelope can be made from different materials having different chemical or physical properties. The shell wall of the envelope of the present invention may have a single layer or multiple layers. When multiple layers are used, different layers can be designed to exhibit different characteristics, such as mechanical properties and rate of degradation.

The shape, size of the absorbable expander and the speed of its absorption in tissue can be so chosen to suit different needs. For example, a small defect or biopsy would require a small scale expander. This tissue repair would occur rapidly and a faster absorbing material would be used (one which loses mechanical strength and mass relatively quickly). On the other hand, a total organ replacement would require a much slower, or incremental development of tissue and thus would require an expander with a slower degradation rate or preferably an expander having a plurality of envelopes that can be sequentially degraded as will be described in detail below.

The implantable device of the present invention also includes means for controlled inflation or deflation of the envelope of the device. Normally, the envelope of the device are in a collapsed configuration. After the device is implanted in a tissue, liquid or gel is introduced into the envelope of the implantable device to inflate or expand the envelope to fill the void in the tissue. As new tissue develops, the envelope is gradually deflated by removing in a controlled manner the liquid or gel from the envelope. Many types of means for inflating or deflating tissue expanders are known in the art and can all be used in the present invention. For example, a conventional injection port or button is most commonly used in the art and can be used in the present invention. Such an injection port normally is connected to the chamber of the expander by a tube or a hollow region which is in fluid communication with the interior of the chamber so as to permit fluid to be injected into, or withdrawn from the envelopes. The injection port may contain a needle-stop of a rigid biocompatible material. The injection port can be mounted on a body surface or imbedded beneath a skin where it can be easily reached by an injection needle. The injection port may be non-absorbable and may be implanted in a location that is convenient for access thereto and removal therefrom. The injection port may also be made bio-absorbable by using bio-absorbable materials. The bio-absorbable injection port may contain a bio-absorbable needle-stop of a rigid bioabsorbable biocompatible material, e.g. polylactide.

Another means for controlled inflation or deflation usable in the present invention is the self-sealing means as disclosed in, e.g., U.S. Pat. No. 5,074,878 to Bark et al. (which is incorporated herein by reference). In this means, the shell wall of the envelope must be made with a needle-penetrable material with self-sealing characteristics. The self-sealing is accomplished when the wall material flows together at the needle opening when the needle is withdrawn from the wall. In such means, if a needle-stop is desired within the chamber, the needle-stop must be made of a bio-absorbable biocompatible material.

Additionally, the deflation of the envelope of the absorbable expander can also be achieved by the bio-absorption of the shell wall of the envelope which leads to the release of the fluid or gel from the envelope into the surrounding environment and subsequently the deflation of the envelope. Other means in the art may also be used which would be apparent to an ordinarily skilled person in the art apprised of the present invention. Preferably, the injection port means is used.

In a preferred embodiment of the present invention, the absorbable tissue expander comprises a plurality of the above-described fluid-tight and semipermeable envelopes and a plurality of means for inflating or deflating each envelope in a controlled fashion. Each envelope may have a separate inflating or deflating means of the types described above, e.g., a port through which liquid or gel and growth factor may be injected as needed. Preferably, the envelopes are insulated from each other by shell walls described above. More preferably, each envelope shares a portion of its shell with another envelope. As a result, when one envelope is deflated other envelopes are not affected. Therefore, individual envelopes can be separately inflated or deflated as needed. In addition, each envelope may be processed to have unique mechanical properties and mass loss profiles, thus allowing sequential biodegradation and absorption of the material, which may lead to sequential deflation of the envelopes through fluid leakage.

The present invention also provides a method of reconstructing tissue using the absorbable tissue expander described above. The method comprises the steps of (1) providing an absorbable tissue expander as described above; (2) implanting the device in the defective area of tissue; (3) inflating the envelope(s) with a biocompatible liquid or gel to create a space for tissue growth; and (4) as new tissue develops surrounding the envelope(s), gradually deflating the envelope(s) to provide sufficient space for further tissue development until the envelope(s) of the device is completely deflated and absorbed by the developed tissue.

The absorbable tissue expander is usually implanted under the skin at a desired area; however, it should be understood that the expander may be used at any site in the body. The tissue expander is usually implanted in a collapsed condition and is inflated by periodic infusions of a liquid fluid or gel into the envelope(s). Suitable liquid or gel for expanding the inflatable envelopes are well known in the art. The liquid or gel should be biocompatible. One exemplary suitable liquid is saline liquid. The liquid or gel may preferably also contain a signal for modifying cell adhesion, growth, or migration, preferably stimulating or promoting the adhesion, growth, or migration of the desired cells, and/or inhibiting the adhesion, growth, or migration of the undesired cells. Suitable signals include but are not limited to growth factors such as epithelial growth factor (EGF), acidic or basic fibroblast growth factor (FGF), vascular endothelial growth factor (VEGF), hepatocyte growth factor (HGF), heparin binding growth factor (HBGF), transforming growth factor (TGF), nerve growth factor (NGF), muscle morphogenic factor (MMP), and platelet derived growth factor (PDGF); extracellular matrix proteins such as fibronectin, collagens, laminins, and vitronectins; and the tri-peptide RGD (arginine-glycine-aspartate) that is found in many of the extracellular matrix proteins. Preferably, compounds which inhibit undesired cells such as cancerous cells and inflammatory cells can also be included. Compounds which prevent infection such as antibiotics can also be included. The release of these agents may be altered by altering the permeability of the expander membrane.

The signals can also be covalently linked to a biocompatible material in the shell wall of the envelope. They can also be associated with the envelope by affinity or any other force. Alternatively, the signals can also be linked to a material that can be covalently linked to or associated by affinity with a biocompatible material in the shell wall of the envelope. The compounds may be able to diffuse through the shell wall at a constant rate to enhance cellular growth around the implant. To replenish these growth factors, upon deflation of the device a "re-charged" volume would be injected into the expander.

Typically, the tissue expander as well as the liquid or gel are sterilized before being delivered into tissue. Methods of sterilizing medical devices and biomedical reagents are generally known in the art. Choosing the appropriate methods known in the art for the purposes of this invention should be apparent to a skilled person in the art.

Tissue growth surrounding the implanted device can be induced by the growth factors included in the device. Alternatively, exogenous cells or three-dimensional constructs containing cells can be transplanted within the space between the envelope and tissue. One suitable example of such a construct is the one described in U.S. patent application Ser. No. 09/058,619 filed Apr. 9, 1998. Serial injections of cell suspension or cell constructs may be conducted. Many different methods of transplanting cells are known in the art and can generally be used for purpose of this invention.

As new tissue grows within the space, the envelope of the invention is gradually deflated by removing a desired amount of the liquid or gel from the envelope so that a desired volume of space for further tissue growth is created. By "gradually" is intended the deflation of an envelope is preferably done in an intermittent fashion until the envelope is fully collapsed. The rate of deflation may vary with a number of factors, e.g., the speed of tissue growth and the amount of cells injected. For example, when a device having a plurality of envelopes is employed, the deflation of each individual envelope may be in a sequential fashion, depending on the tissue growth pattern. The envelopes in the areas where tissue growth is faster are preferably deflated in a faster speed.

Once an envelope is fully deflated, it will be gradually absorbed in situ by the surrounding tissue. This presents a great advantage over conventional expanders in that the envelope of the invention needs not be removed surgically thus avoiding the disruption of the newly formed tissue.

Absorbable expanders can also be designed to contain within the expander and later release a wide variety of biologicals over time including cytokines, growth factors, antineoplastic, chemotherapy agents, adhesion preventing agents and the like.

Chemotherapy agents can be released directly into tumors or adjacent to tumors by small semipermeable expanders that can be placed by minimally invasive surgical or radiological methods. The introduction of chemotherapeutic or other anti-cancer agents by this method provides high concentrations of the agents within the tumor while avoiding the systemic effects of high dose chemotherapy. In a similar manner, small expanders containing rapidly decaying high energy, short half-life radioisotopes can be placed directly into or adjacent to a tumor mass to prevent local irradiation of the tumor.

A variety of cytokines and growth factors can be released by semipermeable expanders into specific sites where they are needed. In cancer patients where immune enhancement is desired, small expanders with specific cytokines and other factors, e.g., tumor antigens, can be placed beneath the skin, in node bearing areas, into the spleen and into tumors to produce immunoreactivity to the tumor. In cases of tissue injury, these devices can be placed in or near bone or other injured tissue to enhance fractures and would healing using growth factors, e.g., bone morphogenetic protein.

Figure 2B:
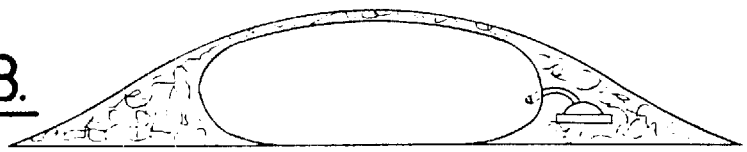
FIG. 2B depicts cells injected into the space for growth into tissue surrounding the absorbable tissue expander device shown in FIG. 2A.
Figure 2C:
FIG. 2C depicts a partially deflated envelope of the absorbable tissue expander device of the present invention.
Figure 2D:
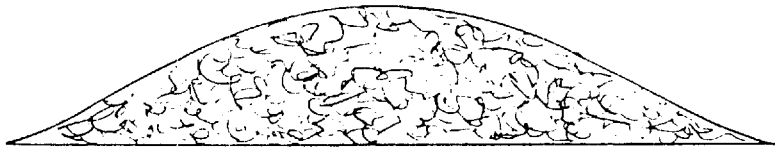
FIG. 2D depicts a fully deflated envelope having been absorbed and integral new tissue being shown in its place.

The present invention is further illustrated by exemplary examples in FIGS. 1 and 2. It is noted that the figures provided herein are for purpose of illustration, and are by no means intended to limit the present invention therewith. Many other embodiments of the invention are possible which would be apparent to an ordinarily skilled person in the art apprised of the present invention.

FIG. 1 depicts two embodiments of the absorbable expander of the present invention having multiple envelopes (only envelopes are shown).

In FIG. 1A, the implantable device 1 has four envelopes 10, 20, 30, and 40 assembled in a coaxial fashion, wherein all four envelopes have a common axial. Envelope 10 is located in the center in a column shape. Envelope 20 circles around envelope 10 and shares a shell wall with envelope 10. Similarly, envelope 30 forms a loop outside envelope 20, and envelope 40 is attached to the outside of envelope 30. Each envelope has its own injection port 14, 24, 34, and 44 respectively. FIG. 1B depicts a cross section view of the device 1 shown in FIG. 1A. In FIG. 1C, the expander 50 comprises a plurality of envelopes 60, 70, 80, 90, 100 and 110 sandwiched together, each having an injection port 64, 74, 84, 94, 104 and 114 respectively for inflation and deflation of the envelope. FIG. 1D is a cross section view of the device of FIG. 1C.

FIG. 2 illustrates the process of reconstructing a tissue such as breast tissue using the absorbable tissue expander device of the present invention. In FIG. 2A, the device 120 has been implanted beneath the skin and subcutaneous tissue. A liquid or gel is injected through the injection port 140 which is connected to the chamber of the envelope 130 with a tube 150 whereby the envelope 130 is fully inflated and the space 160, 160', and 160" are formed. In FIG. 2B, cells are injected into the space for growth into tissue surrounding the device 120. As new tissue grows, the envelope is deflated until it is fully collapsed and the injection port is removed. See FIG. 2C. The fully deflated envelope is eventually absorbed and integral new tissue is formed. See FIG. 2D.

Although the above-described method is directed to using the tissue expander of this invention in tissue reconstruction, it would be apparent to an ordinarily skilled person in the art that the tissue expander of the present invention is fit for many other purposes. For example, it may be used in positioning a particular organ or tissue inside the body. One aspect of this type of applications is that it can be used as a substitute for a traditional tissue expander in bowel displacement. Typically, the tissue expander of the present invention can be implanted near the treatment field thereby displacing the small bowel away from the treatment field. As a result, during the radiation treatment of the cancerous cells in the treatment field, the small bowel which is sensitive to ionizing radiation is not adversely affected by the radiation. Bowel displacement using traditional tissue expanders has been disclosed in, e.g, Armstrong et al. *Int. J. Radiat. Oncol. Bio. Phys.* 19(6):1521–3 (1990); Herbert et al. *Int. J. Oncol. Biol. Phys.* 25:885–893 (1993); Keno et al. *Am. Surg.* 80:473–483 (1994); and Keno et. al., *Oncology*, 12(1): 51–54 (1998), all of which are incorporated herein by reference. The absorbable tissue expander of this invention is superior to the traditional tissue expanders in that after the radiation treatment, the expander need not be removed. It will gradually degrade and eventually be absorbed by the surrounding tissue. It may also be advantageous to use the absorbable tissue expander as a carrier of useful substances such as anti-tumor agents, antibiotics, etc. In that event, the gradual absorption of the tissue expander mass may be associated with the gradual release of these substances for treatment.

Although the foregoing invention has been described in some detail by way of illustration and example for purposes of clarity of understanding, it will be obvious that certain changes and modifications may be practiced within the scope of the appended claims.

That which is claimed is:

1. A method of reconstructing tissue, comprising
   implanting a tissue expander in the tissue, the tissue expander having a plurality of fluid-tight or semipermeable envelopes and means for controlled inflation and deflation of said envelopes, each envelope having a bio-absorbable biocompatible shell defining a chamber and being inflatable upon infusion of a biocompatible liquid or a gel, and deflatable upon removal of said liquid or said gel from said chamber;

inflating said envelopes to form a space therein;
   transplanting cells or cells with biomaterial carriers or biomaterial constructs into said space; and
   gradually deflating said envelopes as the tissue surrounding the envelopes develops to provide space for further tissue development whereby said envelopes are completely deflated and absorbed.

2. The method of reconstructing a tissue according to claim 1, wherein each envelope shares a portion of its shell with another envelope.

3. The method of reconstructing a tissue according to claim 1, wherein said means for controlling inflation and deflation comprises a plurality of injection ports each of which has a hollow region which is in liquid or gel communication with the interior of a chamber.

4. The method of claim 1, wherein said step of deflating said envelopes comprises bio-resorption of the shell and the release of the said biocompatible liquid or gel through said shell.

5. The method of reconstructing a tissue according to claim 1, wherein each envelope has a pre-defined bio-absorption rate in tissue.

6. The method of reconstructing a tissue according to claim 1, wherein said shells are made of materials selected from the group consisting of polyesters, polyanhydrides, polyphosphazenes, polyorthoesters, polyoxalates, polyetheresters, polycarbonates, polycaprolactone, polylactide, copolymer of polylactide and ε-caprolactone, elastomeric polypeptides, mixtures thereof, and composites thereof.

7. The method of reconstructing a tissue according to claim 1, wherein said shells are made of polylactide or lactide/ε-caprolactone copolymer.

8. The method of reconstructing tissue of claim 1, wherein said step of inflating said envelopes with said biocompatible liquid or gel further comprising a signal selected from the group consisting of epithelial growth factor (EGF), acidic or basic fibroblast growth factor (FGF), vascular endothelial growth factor (VEGF), hepatocyte growth factor (HGF), heparin binding growth factor (HBGF), transforming growth factor (TGF), nerve growth factor (NGF), muscle morphogenic factor (MMP), and platelet derived growth factor (PDGF); extracellular matrix proteins such as fibronectin, collagens, laminins, and vitronectins; and the tri-peptide RGD (arginine-glycine-aspartate).

9. A method of reconstructing tissue, comprising:
   implanting a tissue expander in the tissue having a plurality of fluid-tight or semipermeable envelopes and means for controlled inflation and deflation of said envelopes, each envelope having a bio-absorbable biocompatible shell defining a chamber and being inflatable upon infusion of a fluid or a gel, and deflatable upon removal of said fluid or said gel from said chamber;
   inflating said envelopes; and
   gradually deflating said envelopes as the tissue surrounding the said envelopes develops to provide space for further tissue development whereby said envelopes are completely deflated and absorbed.

* * * * *